United States Patent [19]

Sarel

[11] Patent Number: 5,602,283
[45] Date of Patent: Feb. 11, 1997

[54] MULTI-STAGE PROCESS FOR PREPARING N-ALKYL-3,4-DIALKYL-2,6-DINITROANILINES

[75] Inventor: Morris Sarel, Rehovot, Israel

[73] Assignee: Agan Chemical Manufacturers Ltd., Ashdod, Israel

[21] Appl. No.: 447,964

[22] Filed: May 23, 1995

Related U.S. Application Data

[62] Division of Ser. No. 264,450, Jun. 23, 1994, Pat. No. 5,475,148.

[30] Foreign Application Priority Data

Jun. 24, 1993 [IL] Israel .......................... 106118

[51] Int. Cl.$^6$ .................................. C07C 209/18
[52] U.S. Cl. ................. 564/399; 568/584; 568/628; 568/629; 568/630; 568/711
[58] Field of Search .................. 564/399; 568/711, 568/628, 629, 630, 584

[56] References Cited

U.S. PATENT DOCUMENTS

| | | | |
|---|---|---|---|
| 3,658,906 | 4/1972 | Cryer et al. | 564/402 |
| 3,920,742 | 11/1975 | Lutz et al. | 564/441 |
| 4,395,572 | 7/1983 | Chan | 564/399 |
| 4,723,043 | 2/1988 | Ratton | 568/709 |
| 5,093,526 | 3/1992 | Sharvit et al. | 564/399 |

FOREIGN PATENT DOCUMENTS

| | | |
|---|---|---|
| 519842 | 12/1981 | Australia . |
| 0211775 | 2/1987 | European Pat. Off. . |
| 0518151 | 12/1992 | European Pat. Off. . |
| 6953 | 5/1969 | France . |
| 2077608 | 10/1971 | France . |
| 2319610 | 2/1977 | France . |

OTHER PUBLICATIONS

Hartshorn et al, "The nitration of 4–methylphenol, 3,4–dimethylphenol and 3,4,5–trimethylphenol with nitrogen dioxide", *Chemical Abstracts*, vol. 112, No. 9, p. 735, Feb. 26, 1990.

Chemical Abstracts 94: 169422r "Dinitrobenzene herbicides" (1981).

Chemical Abstracts 101: 54701b "Ortho substituted phenols" (1984).

Chastrette et al "Structure–odor relationships using neural networks", *Eur. J. Med. Chem.*, 26:829–833 (1991).

*Primary Examiner*—Brian M. Burn
*Attorney, Agent, or Firm*—Browdy and Neimark

[57] ABSTRACT

A multistage process of preparing N-alkyl-3,4-dialkyl-2,6-dinitroanilines starts from 3,4-dialkyl phenol and goes through the stages of 3,4-dialkyl-2,6-dinitrophenol and 3,4-dialkyl-2,6-ditro alkoxybenzene, wherein the latter are new compounds.

28 Claims, No Drawings

MULTI-STAGE PROCESS FOR PREPARING N-ALKYL-3,4-DIALKYL-2,6-DINITROANILINES

This is a division of parent application Ser. No. 08/264,450, filed Jun. 23, 1994 (now U.S. Pat. No. 5,475,148).

BACKGROUND OF THE INVENTION

The present invention concerns the improved process for preparing N-alkyl-3,4-dialkyl-2,6-dinitroanilines. The present invention more particularly concerns a commercially viable process to prepare the compound pendimethalin, (known by the chemical name N-(1-ethylpropyl)-2,6-dinitro-3,4-xylidine) its derivatives and its intermediates.

Pendimethalin and its derivatives are reported by U.S. Pat. No. 4,066,441 as excellent pre-emergent herbicides.

Several procedures are reported in the literature to prepare these compounds. The last step in preparing the compound pendimethalin is reported by U.S. Pat. No. 3,920,742 to involve the nucleophilic substitution of 3,4-dimethyl-2,6-dinitrohalobenzene (especially the chloro derivatives) with the appropriate amine, thus:

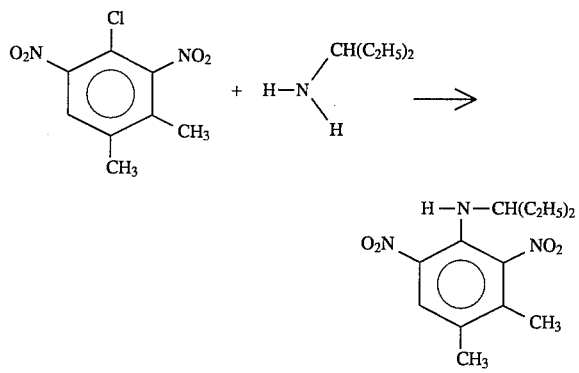

where the chloro-intermediate was prepared in one of several problematic multi-step processes beginning with o-xylene, as follows:

o-Xylene is first chlorinated to form 4-chloro-o-xylene, which in turn is nitrated with fuming nitric acid to give the 3,4-dimethyl-2,6-dinitro-chlorobenzene in a yield of 27%. First of all, the low yield is not commercially viable. Secondly, the chlorination step affords a mixture of chloro isomers, requiring the distillation of the product mixture to separate the 4-chloro- isomer from its 3-chloro isomer with only great difficulty due to their very close boiling points. Finally, the low yield of the nitration step stems from the need to purify the 3,4-dimethyl-2,6-dinitro-chlorobenzene from dangerous higher nitrated by products. This alone makes this process difficult for commercialization.

A second process, illustrated by U.S. Pat. No. 4,123,250, involves nitrating 3,4-dimethylaniline to form 3,4-dimethyl-2,6-dinitroaniline which is then reacted via a Sandmeyer reaction to form 3,4-dimethyl-2,6-dinitro-chlorobenzene. This process suffers from low yields and requires the laborious separation from various by-products.

A third process, illustrated by U.S. Pat. No. 4,199,669 and U.S. Pat. No. 4,261,926, is based on the reductive alkylation of 3,4-dimethylaniline with a ketone or directly from 4-nitro-o-xylene, thus:

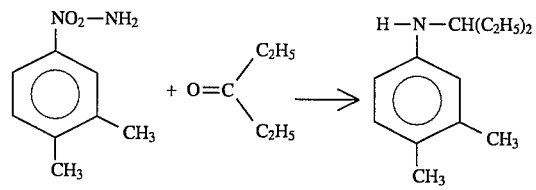

and the product is subsequently nitrated with concentrated nitric acid to give the 2,6-dinitro derivative. This process suffers from the fact that the preparation of the 4-nitro-o-xylene always is accompanied by the 3-nitro derivative, and their separation is very difficult.

Several improvements have been reported in attempts to overcome the above described problems. Thus, U.S. Pat. No. 3,929,916 and U.S. Pat. No. 3,929,917 disclosed the use of mercury salts or nitrogen tetroxide to avoid the formation of unwanted by-products. However, these catalysts are poisonous and dangerous materials requiring special handling.

U.S. Pat. No. 4,119,669 and U.S. Pat. No. 4,201,926 report the use of noble metal catalysts. But such catalysts are very expensive with losses during the process.

According to U.S. Pat. No. 4,136,117; and U.S. Pat. No. 4,621,157 the nitration of N-alkyl-zylidine leads to three products:

1. N-Alkyl-3,4-dimethyl-2,6-dinitroaniline:
2. N-Nitroso-N-alkyl-3,4-dimethyl-2,6-dinitroaniline; and
3. N-Nitro-N-alkyl-3,4-dimethyl-2,6-dinitroaniline.

The formation of toxic nitroso compounds makes it imperative to lower the concentration of these compounds to very low levels. As a result, a denitrosation process (as described in U.S. Pat. No. 4,134,917 and U.S. Pat. No. 4,136,117) and denitration process (as described in U.S. Pat. No. 4,391,992) are required in order to obtain commercially useful product. However, it is preferable to use a process to prepare pendimethalin and its analogues which avoids the formation of such toxic nitroso compounds.

OBJECTIVES OF THE INVENTION

It is the objective of the present invention to provide a new and improved method for the preparation of N-alkyl-3,4-dialkyl-2,6-dinitroanilines and their intermediates. It is a further objective of the present invention to provide a method for the preparation of these compounds avoiding the above mentioned disadvantage without having to handle highly toxic or dangerous compounds. A further objective is the provision of a commercially viable method for the preparation of these compounds in high yields.

SUMMARY OF THE INVENTION

It has unexpectedly been discovered that N-alkyl-3,4-dialkyl -2,6-dinitroanilines of the formula

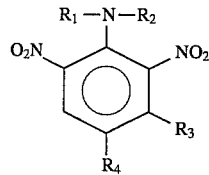

Wherein $R_1$ is hydrogen, $C_1$ to $C_6$ straight or branched chain alkyl group and $R_2$, $R_3$ and $R_4$, are independently $C_1$ to $C_6$ straight or branched chain alkyl group optionally substituted by one or more halogen groups, may be prepared comprising the steps of:

1. Reacting 3,4-dialkyl phenol with nitric acid in a two phase system to form 2,6-dinitro-3,4-dialkyl phenol;
2. Alkylating the 2,6-dinitro-3,4-dialkyl phenol by reacting with an alkylating agent preferably in the presence of a catalytic amount of a phase transfer catalyst chosen from the group consisting of $(R')_4Q^+X^-$ wherein R' may be the same or different $C_1$ to $C_{16}$ straight or branched alkyl groups, benzyl, substituted benzyl;

Q is N or P: and

X is Cl, Br, I or $HSO_4$:

a macrocyclic ether and polyethylene glycols of formula $HO-(CH_2CH_2O-)_n-CH_2CH_2OH$ where n is an integer from 10 to 50 to form 2,6-dinitro-3,4-dialkyl alkoxy benzene.

3. Reacting the 2,6-dinitro-3,4-dialkyl alkoxy benzene with an amine in the presence of a catalytic amount of base or halide to form N-alkyl-3,4-dialkyl-2,6-dinitroaniline; and
4. Recovering the N-alkyl-3,4-dialkyl-2,6-dinitroaniline formed.

DETAILED DESCRIPTION OF THE INVENTION

The reaction process is generally illustrated below on a batch-wise basis:

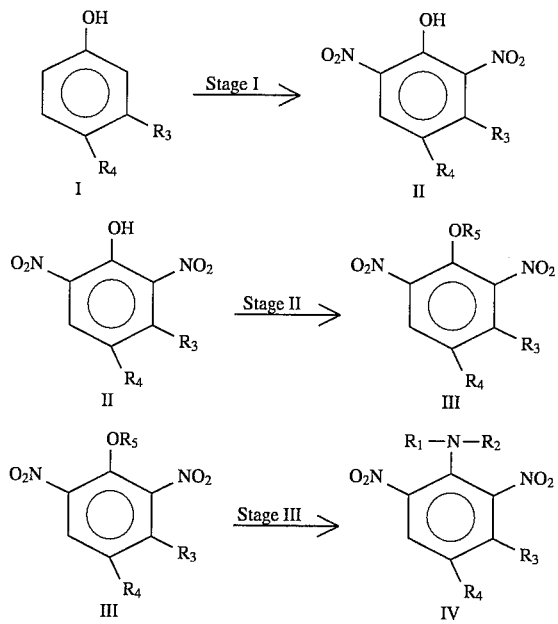

Examples of alkyl groups of groups $R_1$, $R_2$, $R_3$, $R_4$ and $R_5$ are methyl, ethyl, propyl, butyl, pentyl, hexyl, isopropyl, isobutyl, 1-methyl propyl, 1-ethyl propyl, 1-methylbutyl, 1-ethylbutyl, and the like.

Stage I involves a direct and improved process to nitrate 3,4-dialkyl phenol with a minimum of by-products. This is effected using a two-phase system of an organic solvent and an aqueous nitric acid solution. Nitration of phenols using a two phase system has already been disclosed in East German Patent Number 12,348; West German Patent Number 1,092, 025; and U.S. Pat. Nos. 2,802,883 and 4,621,157 using different conditions and different phenols.

In practice, a solution of 3,4-dialkyl phenol in an organic solvent is slowly added to the aqueous solution of nitric acid at a temperature of from 10° C. to 40° C. over a period of 3 to 6 hours. The molar ratio of phenol to nitric acid may be 1:2 to 1:4, but preferably from 1:2 to 1:2.5. The reaction is carried out preferably at atmospheric pressure, when the concentration of nitric acid may be 15% to 55%, preferably 20% to 50%.

The organic water-imiscible solvent may be any chlorinated aliphatic or aromatic derivative the phenol is soluble in. Examples are dichloromethane, 1,2-dichloroethane, 1,1, 1-trichloroethane, carbon tetrachloride, chloroform, trichloroethylene, tetrachloroethylene, chlorobenzene, dichlorobenzene, benzene, dialkylethers and mixtures of these.

The resulting reaction mixture may be worked up by separating the two phases and the nitrated product in the organic phase is separated by standard means. The aqueous acidic phase may be reused in this process after adjusting the concentration with fresh concentrated nitric acid.

The 3,4-dialkyl phenol may be either commercially available, as in the case of 3,4-xylenol or prepared from 3,4-dialkyl benzenesulfonic acid as described in SU 577,202 and CZ 159,631. The 3,4-dialkyl benzenesulfonic acid may be prepared by the sulfonation of o-dialkyl benzene according to Czech Patent Number 163,030.

Stage II involves an alkylation of the hydroxylic group, namely O-alkylation. This reaction can be carried out using alkylating agents such as alkyl sulfate, alkylarylsulfonates or alkyl halides. Dimethyl and diethyl sulfates are preferred. The reaction is carried out in the presence of bases such as alkali hydroxides, alkali carbonates, or alkali hydrogen carbonates, with alkali carbonates preferred.

The second stage is preferably run in the presence of a phase transfer catalyst. Preferred examples are tetra(aralkyl)-alkylammonium halides such as didecyldimethyl ammonium chloride, tricaprylmethyl ammonium chloride, benzyltrimethyl ammonium chloride, tetrabutyl ammonium chloride, triethylbenzyl ammonium chloride and the like. Most preferred are didecyldimethyl ammonium chloride, tricaprylmethyl ammonium chloride and triethylbenzyl ammonium chloride.

This stage is carried out in an organic solvent. This solvent may be an aliphatic ketone (as acetone, methylethyl ketone, methylisobutyl ketone and the like), a cycloalkylketone (as cyclohexanone, cyclopentanone and the like), haloalkanes (as dichloromethane, 1,2-dichloroethane, methylchloroform, carbon tetrachloride and the like), an aromatic hydrocarbon (as benzene, toluene, xylene and the like), a cycloalkane as cyclohexane and mixtures of these. Haloalkanes are preferred with 1,2-dichloroethane most preferred.

The reaction of Stage II is run at a temperature of from 40° C. to 90° C., preferably from 60° C. to 80° C.

Stage III involves the reaction of the alkoxy 2,6-dinitro-3,4-dialkyl benzene in a nucleophilic substitution ($SN_r$) with the appropriate amine. The reaction is run neat (no solvent) with a molar ratio of amine to phenol derivative of from 2:1 to 6:1, preferably from 3:1 to 5:1, at a temperature of from 20° C. to 40° C. The excess amine can be reused after distilling off at the end of the reaction.

The reaction of Stage III was found to be catalyzed by bases chosen from the group consisting of alkali hydroxide (as sodium hydroxide, potassium hydroxide, lithium hydroxide), and halogenides as (calcium chloride, barium bromide and lithium chloride preferably calcium chloride) by lowering the reaction time to about 24 hours. The amount of catalyst added is one mole percent to 6 mole percent, preferably 3 mole percent to 5 mole percent, catalyst per mole alkoxy benzene derivative.

While the invention will now be described in connection with certain preferred embodiments in the following examples, it will be understood that it is not intended to limit the invention to these particular embodiments. On the contrary, it is intended to cover all alternatives, modifications and equivalents as may be included with the scope of the invention as defined by the appended claims. Thus, the following examples which include preferred embodiments will serve to illustrate the practice of this intention, it being understood that the particulars shown are by way of example and for purposes of illustrative discussion of preferred embodiments of the present invention only and are presented in the cause of providing what is believed to be the most useful and readily understood description of procedures as well as of the principles and conceptual aspects of the invention.

EXAMPLE 1

Preparation of 2,6-dinitro-3,4-xylenol

A mixture of 630 grams (5 moles/ of a 50% aqueous nitric acid and 400 ml dichloromethane were introduced in a two liter flask fitted with a stirrer, a reflex condenser, a dropping funnel and a thermometer. To this stirred mixture was added dropwise a solution of 245 g (2 moles) 3,4-xylenol in 400 ml dichloromethane, during two hours, maintaining the temperature at 20°–25° C. After another hour stirring at the same temperature the reaction mixture was heated to reflux (about 40° C.) until the starting product and the two intermediate products (2-nitro-3,4-xylenol and 4-nitro-3,4-xylenol) have disappeared (followed by GC analysis). This occurs in about three hours. The mixture was cooled to ambient temperature and allowed to separate in two phases. The lower organic phase was separated from the aqueous acidic layer and washed twice with water. Water (400 ml) was added to the organic phase and dichloromethane was removed by distillation. The slurry of the dinitro compound in water was cooled and filtered and dried at 70° C. A product of 93.7%. 2,6-dinitro-3,4-xylenol pure was obtained which was 74.5% of the theoretical yield. After crystallization from ethyl alcohol it has a melting point of 124°–125° C.

EXAMPLE 2

Example 1 was repeated but, after washing of the organic phase with water, the dichloromethane was recovered by distillation leaving the residue of 2,6-dinitro-3,4-xylenol. The crude product was dissolved in a 6 percent solution of sodium hydroxide and thereafter acidified with 3,5-N-hydrochloric acid. The precipitated solid was filtered, washed with water and dried at 70° C. It was obtained as product with melting point of 120°–122° C.

EXAMPLE 3

Preparation of 2,6-dinitro-3,4-dimethyl anisole

A solution of 226 g, 2,6-dinitro-3,4-xylenol, 93.7%. (1 mole) in two liters 1,2-dichloroethane was placed in a three liter reaction flask. Sodium carbonate 128 g (1.2 moles) and 0.81 g Didecyldimethyl-ammonium chloride (DDAC) were added to the above solution and afterwards 151.3 (1.2 moles) of dimethylsulfate were introduced during 15 minutes at the ambient temperature. The reaction mixture was heated with stirring to reflux during two hours. Water (400 ml) was added and heating was continued for another hour. This mixture was cooled to 25° C. and allowed to separate in two phases. The lower organic phase was separated, washed with water to neutral.

The solvent was next recovered by distillation and the remaining oily product solidified by cooling. A product (225.8 g) of 94%. 2,6-dinitro-3,4-dimethylanisole was obtained at a 93.9% of the theoretical yield based on 2,6-dinitro-3,4- xylenol consumed. Crystallization from ethyl alcohol gave a product with a melting point of 67.3°–67.6° C.

EXAMPLE 4

Example 3 was repeated in every detail except that sodium carbonate was replaced by potassium carbonate. The yield of 2,6-dinitro-3,4-dimethylanisole was 95%.

EXAMPLE 5

Example 4 was repeated except that didecyldimethylammonium chloride was replaced with tricaprylmethyl ammonium chloride (Aliquat 336). The yield obtained was essentially the same.

EXAMPLE 6

Preparation of 2,6-dinitro-3,4-dimethylanisole 2,6-dinitro-o-xylenol (0.1 mole) was dissolved in 200 ml acetone to which 0.12 moles potassium carbonate and 0.4 g triethylbenzylammonium chloride were added. Next 0.12 mole dimethylsulfate were added during ten minutes and the mixture was heated to reflux during 1 hour. Water (40 ml) and 7 g potassium carbonate were added to the reaction mixture and heating to reflux was continued for half an hour. Acetone was removed from the reaction mixture by distillation and to the residue were added with stirring 80 ml DCM and 100 ml water. The organic phase was washed with water to neutral and evaporated to obtain the 2,6-dinitro-3,4-dimethyl anisole with a yield of 94%.

EXAMPLE 7

Preparation of 2,6-dinitro-3,4-dimethylphenetol

Example 5 was repeated except that 2,6-dinitro-3,4-xylenol was reacted with diethylsulphate 185 g (1.2 mole). There was obtained 2.6 dinitro-3,4-dimethyl phenetole with a yield of 94%. Crystallization from ethyl alcohol gave a product with a melting point of 64°–66° C.

EXAMPLE 8

Preparation of N(1-ethylpropyl)-2,6-dinitro-3,4 xylidine

To a suitable reaction vessel equipment with a thermometer and mechanical stirrer was introduced 24 g 2,6-dinitro-3,4-dimethylanisole 94% (0.1 moles), 0.55 g $C_aCl_2$ (0.005 moles), and 43.5 g (0.5 moles) 1-ethyl propylamine. The reaction mixture was stirred at a temperature of 25°–30° C. The progress of the reaction was followed by periodically withdrawing samples and analyzing for starting product and the new product formed. During 24 hours the starting product disappeared and the N-(1-ethylpropyl)-3,4-dimethyl-2,6-dinitroaniline is gradually formed. After completion of the reaction as indicated by vapor phase chromatography, the excess of 1-ethyl-propylamine was recovered from the reaction mixture by distillation. The residue was dissolved in dichloromethane and the solution was successively washed with 5% aqueous hydrochloric acid, 5% aqueous sodium hydroxide and then by water to neutral and dried. The solvent is next recovered by distillation leaving an oily product which solidified. (25.2 g 96.6%) with a yield of 86.6%.

EXAMPLE 9

The procedure of Example 8 was repeated but when the reaction was completed the mixture was poured into a solution of 10% aqueous hydrochloric acid with cooling and stirring. The insoluble N-(1-ethylpropyl)2,6 dinitro 3,4-xylidine was extracted with 50 ml dichloromethane and washed with a 5% aqueous sodium hydroxide followed by washing with water to neutral. Removal of dichloromethane left the desired product. The excess of 1-ethyl propylamine was recovered as the solid chlorohydrate by evaporation of the aqueous solution.

EXAMPLE 10

Example 8 was repeated in every detail except that 2,6-dinitro-3,4-dimethyl phenetole was reacted with 1-ethylpropylamine in the presence of 5% mole lithium chloride as catalyst. The yield was essentially the same.

We claim:

1. A process for preparing N-alkyl-3,4-dialkyl-2,6-dinitroanilines of the formula

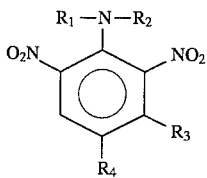

wherein $R_1$ is hydrogen, $C_1$ to $C_6$ straight or branched chain alkyl group; and $R_2$, $R_3$ and $R_4$ are independently $C_1$ to $C_6$ straight or branched chain alkyl group optionally substituted by one or more halogen groups, characterized in that a. a 3,4-dialkyl phenol of the formula

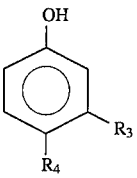

is selectively nitrated with nitric acid in stage I in a two phase system to form 3,4-dialkyl-2,6-dinitrophenol of the formula:

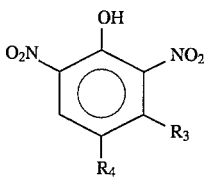

b. the 3,4-dialkyl-2,6-dinitrophenol in stage II is alkylated with an alkylating agent in the presence of a base and a catalytic amount of a phase transfer catalyst selected from the group consisting of

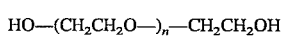

wherein

R' may be the same or different $C_1$ to $C_{16}$ straight or branched alkyl groups, benzyl, substituted benzyl;

Q is N or P; and

X is Cl, Br, I or $HSO_4$;

a macrocyclic ether and polyethylene glycols of formula $$HO-(CH_2CH_2O-)_n-CH_2CH_2OH$$

where n is an integer from 10 to 50, in an organic solvent to form 3,4-dialkyl-2,6-dinitro alkoxybenzene of the formula:

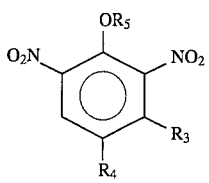

where $R_5$ is an alkyl group having 1 to 6 carbon atoms;

c. the 3,4-dialkyl-2,6-dinitro alkoxybenze is reacted in stage III with an amine of the formula

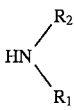

where $R_1$ and $R_2$ are defined above, in the presence of a catalytic amount of base or halide to form N-alkyl-3,4-dialkyl-2,6-dinitroaniline; and d. the N-alkyl-3,4-dialkyl-2,6-dinitroaniline is recovered.

2. A process in accordance with claim 1 wherein the mole ratio of phenol to nitric acid in Stage I is from 1:2 to 1:4.

3. A process in accordance with claim 1 wherein the mole ratio of phenol to nitric acid in Stage I is from 1:2 to 1:2.5.

4. A process in accordance with claim 1 wherein the solvent of Stage I is chosen from the group consisting of dichloromethane, 1,2-dichloroethane, 1,1,1-trichloroethane, carbon tetrachloride, chloroform, trichloroethylene, tetrachloroethylene, chlorobenzene, dichlorobenzene, benzene, dialkylether and mixtures of these.

5. A process in accordance with claim 4 wherein the solvent of Stage I is dichloromethane.

6. A process in accordance with claim 1 wherein the alkylating agent of Stage II is selected from the group consisting of alkyl sulfate, alkylarylsulfonate, or alkyl halides.

7. A process in accordance with claim 6 wherein the alkylating agent of Stage II is dimethylsulfate or diethylsulfate.

8. A process in accordance with claim 1 wherein the phase transfer catalyst of Stage II is an alkyl or aralkylammonium halide.

9. A process in accordance with claim 8 wherein the phase transfer catalyst of Stage II is didecyldimethylammonium chloride, tricaprylmethyl ammonium chloride, or triethylbenzyl ammonium chloride.

10. A process in accordance with claim 1 wherein the solvent of Stage II is selected from the group consisting of acetone, methylethyl ketone, methyisobutyl ketone, cyclohexanone, cyclopentanone, dichloromethane, 1,2-dichloroethane, methylchloroform, carbon tetrachloride, benzene, toluene, xylene, cyclohexane and mixtures of these.

11. A process in accordance with claim 10 wherein the solvent of Stage II is dichloroethane or acetone.

12. A process in accordance with claim 1 wherein the amine of Stage III is a monoalkylamine.

13. A process in accordance with claim 1 wherein the mole ratio of amine to alkoxybenzene derivative of Stage III is from 2:1 to 6:1.

14. A process in accordance with claim 1 wherein the mole ratio of amine to alkoxybenzene derivative of Stage III is from 3:1 to 5:1.

15. A process in accordance with any of claim 1 wherein the catalyst of Stage III is selected from the group consisting of sodium hydroxide, potassium hydroxide, lithium hydroxide, calcium chloride, barium bromide and lithium chloride.

16. A process in accordance with any of claim 15 wherein the catalysts of Stage III is calcium chloride or lithium chloride.

17. A process for preparing N-alkyl-3,4-dialkyl-2,6-dinitroaniline of the formula

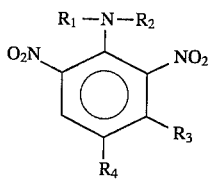

wherein $R_1$ is hydrogen, $C_1$ to $C_6$ straight or branched chain alkyl group; and $R_2$, $R_3$ and $R_4$ are independently $C_1$ to $C_6$ straight or branched chain alkyl group optionally substituted by one or more halogen groups, characterized in that a. a 3,4-dialkyl-2,6-dinitrophenol of the formula

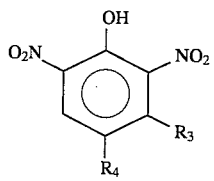

is alkylated with an alkylating agent in stage I in the presence of a base and a catalytic amount of a phase transfer catalyst selected from the group consisting of (R')$_4$Q$^+$X— wherein

R' may be the same or different $C_1$ to $C_{16}$ straight or branched alkyl groups, benzyl, substituted benzyl;

Q is N or P; and

X is Cl, Br, I or HSO$_4$;

a macrocyclic ether and polyethylene glycols of formula

HO—(CH$_2$CH$_2$O—)$_n$—CH$_2$CH$_2$OH where n is an integer from 10 to 50, in an organic solvent to form 3,4-dialkyl-2,6-dinitro alkoxybenzene of the formula:

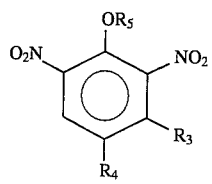

where $R_5$ is an alkyl group having 1 to 6 carbon atoms;

b. the 3,4-dialkyl-2,6-dinitro alkoxybenze is reacted in stage II with an amine of the formula

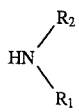

where $R_1$ and $R_2$ are defined above, in the presence of catalytic amount of base to form N-alkyl-3,4-dialkyl-2,6-dinitroaniline; and c. the N-alkyl-3,4-dialkyl-2,6-dinitroaniline is recovered.

18. A process in accordance with claim 17 wherein the alkylating agent of Stage II is selected from the group consisting of alkyl sulfate, alkylarylsulfonate, or alkyl halides.

19. A process in accordance with claim 18 wherein the alkylating agent of Stage II is dimethylsulfate or diethylsulfate.

20. A process in accordance with claim 17 wherein the phase transfer catalyst of Stage II is an alkyl or aralkylammonium halide.

21. A process in accordance with claim 20 wherein the phase transfer catalyst of Stage II is didecyldimethylammonium chloride tricapylmethyl ammonium chloride, or triethylbenzylammonium chloride.

22. A process in accordance with claim 17 wherein the solvent of Stage II is selected from the group consisting of acetone, methylethyl ketone, methyisobutyl ketone, cyclohexanone, cyclopentanone, dichloromethane, 1,2-dichloroethane, methylchloroform, carbon tetrachloride, benzene, toluene, xylene, cyclohexane and mixtures of these.

23. A process in accordance with claim 22 wherein the solvent of Stage II is dichloroethane or acetone.

24. A process in accordance with claim 23 wherein the amine of Stage III is a monoalkylamine.

25. A process in accordance with claim 17 wherein the mole ratio of amine to alkoxybenzene derivate of Stage III is from 2.1 to 6.1.

26. A process in accordance with claim 17 wherein the mole ratio of amine to alkoxybenzene derivative of Stage III is from 3.1 to 5.1.

27. A process in accordance with claim 17 wherein the catalyst of Stage III is selected from the group consisting of sodium hydroxide, potassium hydroxide, lithium hydroxide, calcium chloride, barium bromide and lithium chloride.

28. A process in accordance with claim 27 wherein the catalyst of Stage III is calcium chloride or lithium chloride.

* * * * *